(12) United States Patent
Zribi et al.

(10) Patent No.: US 9,395,324 B2
(45) Date of Patent: Jul. 19, 2016

(54) THIN FILM MICROMACHINED GAS SENSOR

(75) Inventors: Anis Zribi, Colorado Springs, CO (US); Ken Mott, Colorado Springs, CO (US)

(73) Assignee: UTC FIRE & SECURITY CORPORATION, Farmington, CT (US)

( * ) Notice: Subject to any disclaimer, the term of this patent is extended or adjusted under 35 U.S.C. 154(b) by 631 days.

(21) Appl. No.: 13/994,584

(22) PCT Filed: Dec. 14, 2010

(86) PCT No.: PCT/US2010/060320
§ 371 (c)(1),
(2), (4) Date: Jun. 14, 2013

(87) PCT Pub. No.: WO2012/082113
PCT Pub. Date: Jun. 21, 2012

(65) Prior Publication Data
US 2013/0277217 A1    Oct. 24, 2013

(51) Int. Cl.
*G01N 27/407* (2006.01)

(52) U.S. Cl.
CPC .................. *G01N 27/4074* (2013.01)

(58) Field of Classification Search
CPC ............ G01N 27/407; G01N 27/4071; G01N 27/4074; G01N 27/4075
See application file for complete search history.

(56) References Cited

U.S. PATENT DOCUMENTS

| 5,401,376 | A | 3/1995 | Foos et al. |
| 5,573,648 | A * | 11/1996 | Shen ............. G01N 33/004 |
| | | | 204/412 |
| 6,200,443 | B1 | 3/2001 | Shen et al. |
| 7,404,882 | B2 | 7/2008 | Prohaska et al. |
| 7,704,356 | B2 | 4/2010 | Kuhn |

OTHER PUBLICATIONS

Zribi et al., Micromachined resonant multiple gas sensor, Sensors and Actuators A 122, pp. 31-38 (2005).*

* cited by examiner

*Primary Examiner* — Luan Van
*Assistant Examiner* — Maris R Kessel
(74) *Attorney, Agent, or Firm* — Cantor Colburn LLP

(57) ABSTRACT

A thin film/MEMS electrochemical gas sensor includes a body having first and second joined subassemblies to form an interior portion of the body, and is composed of a semiconductor material. The body includes at least one opening configured to allow air to pass into the interior portion of the body. A membrane stack is located in the interior of the body, producing an electrical signal that represents a concentration of target gas in the air at the membrane stack. Conductive contacts are configured to provide electrical connection to the membrane stack to access the electrical signal produced by the membrane stack.

20 Claims, 3 Drawing Sheets

THIN FILM MICROMACHINED GAS SENSOR

BACKGROUND

The present invention relates to a compact gas (e.g., carbon monoxide) sensor formed at least partially of a thin film material such as silicon.

Carbon monoxide (CO) is an example of a gas of interest to be sensed, as it is a colorless, odorless, highly toxic gas that is dangerous to humans at fairly low concentrations. CO is a commonly generated gas during early stages of combustion or heating of various materials. Detecting CO (or other gases) can be accomplished using numerous techniques including spectroscopy, electrochemical sensing, and metal oxide semiconductor (MOS) devices. Existing electrochemical CO sensors provide high performance but are relatively bulky.

Miniature devices fabricated from semiconductor materials such as silicon have become known as micro-electromechanical systems (MEMS). MEMS processing techniques allow fabrication of very small devices with high resolution.

SUMMARY

The present invention is a thin film/MEMS electrochemical gas sensor that includes a body having first and second joined subassemblies to form an interior portion of the body. The body is composed of a semiconductor material, and includes at least one opening configured to allow air to pass into the interior portion of the body. A membrane stack is located in the interior of the body, producing an electrical signal that represents a concentration of the target gas in the air at the membrane stack. Conductive contacts are configured to provide electrical connection to the membrane stack to access the electrical signal produced by the membrane stack.

DETAILED DESCRIPTION

An electrochemical gas sensor for sending a target gas (such as a toxic gas) is a type of fuel cell that, rather than being configured to produce power, is configured to produce an electrical signal (current or voltage) that is related to the amount of target gas in the atmosphere. Measurement of the electrical signal gives a measure of the concentration of the target gas analyte in the atmosphere. The gas sensor includes an ion conducting proton exchange membrane positioned between and in electrical contact with first and second electrodes. Introduction of the gas to the first electrode produces an electrochemical reaction facilitated by the presence of a catalyst, where the gas molecules are oxidized into other molecules, and protons and electrons are generated by the reaction. For example, if the gas introduced is carbon monoxide (CO), the CO molecules are oxidized into carbon dioxide ($CO_2$). The protons, which are ions of hydrogen, migrate across the proton exchange membrane to the second electrode, where they react with electrons and oxygen to form water in a reduction reaction. The electrochemical reaction generates an electrical signal which is proportional to the concentration of gas at the first electrode. More details of an exemplary electrochemical gas sensor (in particular, a CO sensor) are disclosed in U.S. Pat. No. 6,200,443.

In existing electrochemical gas (e.g., CO) sensors as described generally above, a reservoir containing an electrolyte (e.g., water) of several cubic centimeters is employed to hydrate the proton exchange membrane, which dictates the typical size of such sensors to be at least about 5 centimeters high and 2 centimeters in diameter. Also, in a sensor of this size, the response time of the sensor can be an issue due to the length of the diffusion path from the membrane to the electrodes. Moreover, it can be difficult in these sensors to achieve consistent alignment and contact between the membrane and the electrodes, due to the crimping techniques that are employed to press the membrane and the electrodes together. A gas (e.g., CO) sensor employing electrochemical sensing techniques that has reduced size and response time, and increased accuracy with more consistent and precise contact between the membrane and the electrodes would be an improvement to the state of the art. Various embodiments of a miniature thin film micromachined gas sensor are disclosed herein.

Figure 1:
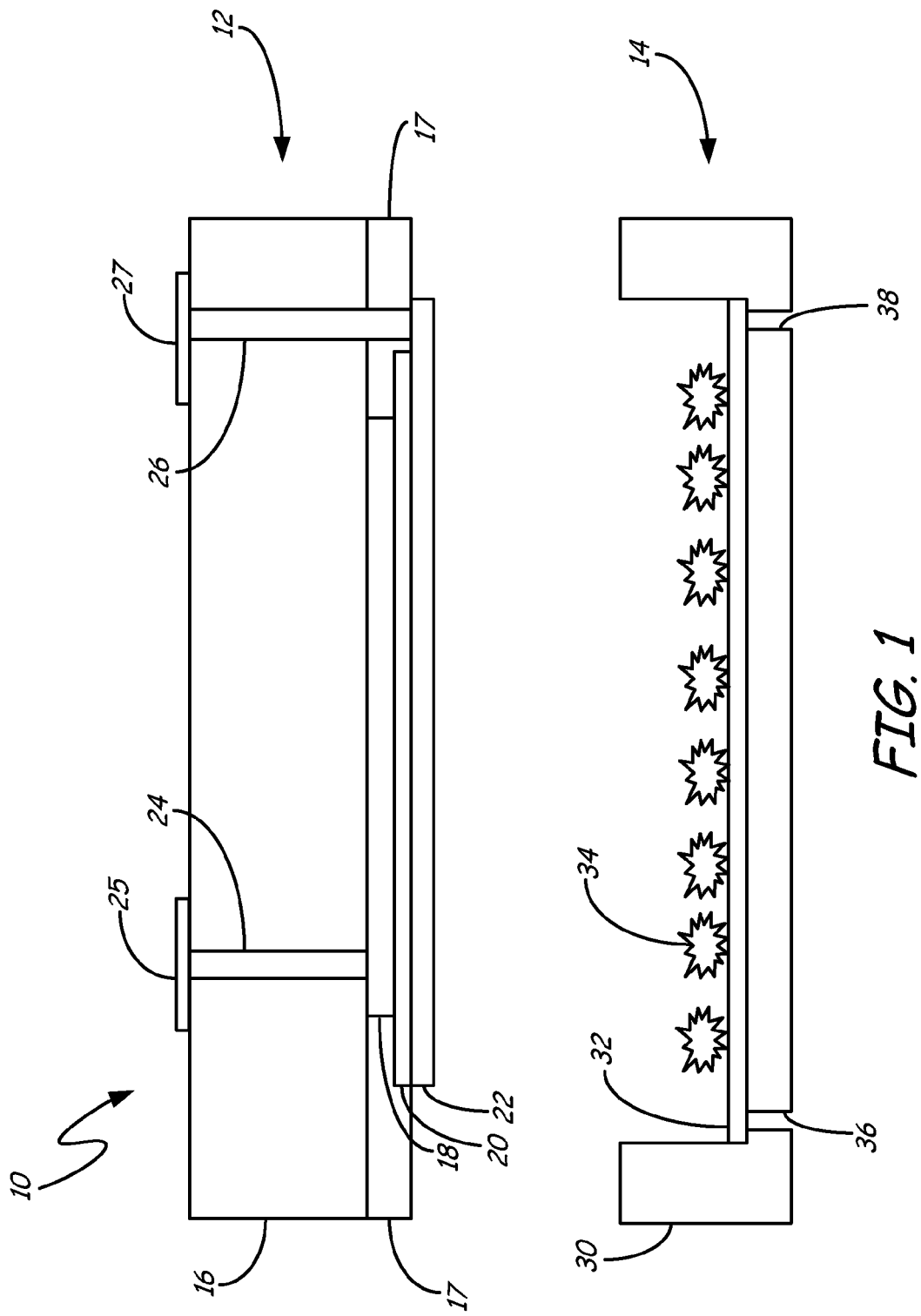
FIG. 1 is a diagram illustrating a thin film/MEMS gas sensor according to an embodiment of the present invention.

FIG. 1 is a diagram illustrating thin film gas sensor 10 according to an embodiment of the present invention. The description of sensor 10 that follows describes a particular embodiment in which sensor 10 is a CO sensor, although embodiments for detecting other target gases (such as toxic gases) will be similar in many respects. Sensor 10 includes first thin film subassembly 12 and second thin film subassembly 14. First thin film subassembly 12 is made up of semiconductor wafer 16, formed of silicon or a similar material, dielectric layer 17, and a membrane stack that includes top electrode membrane 18, proton exchange membrane 20, and bottom electrode membrane 22. Dielectric layer 17 may be composed of a material such as silicon dioxide ($SiO_2$), a silicon nitride ($Si_xN_y$) dielectric, or others. Top electrode membrane 18 and bottom electrode membrane 22 are semipermeable electrically conductive membranes, such as carbon membranes. Proton exchange membrane 20 may be a proton conductive membrane of a perfluorosulfate ionomer, for example, a NAFION® membrane supplied by DuPont, with composite catalytic electrodes. The composite catalytic electrodes include an electrode material coated with a catalyst coating that facilitates electrochemical reaction, reducing the energy required for the reaction to occur. For example, in a CO sensor, the catalyst coating is a platinum alloy. Conductive via 24 extends through semiconductor wafer 16 to provide electrical contact between top electrode membrane 18 and contact pad 25, and conductive via 26 extends through semiconductor wafer 16 and dielectric layer 17 to provide electrical contact between bottom electrode membrane 22 and contact pad 27. Contact pads 25 and 27 may be composed of a conductive metal such as aluminum, copper, nickel, gold, or others.

Second thin film subassembly 14 is made up of semiconductor wafer 30, a filter film realized in the exemplary embodiment shown in FIG. 1 as activated carbon film 32, and hygroscopic material 34. Semiconductor wafer 30 may be formed with the geometry shown by high resolution MEMS processing techniques such as reactive ion etching, chemical anisotropic etching, or others, and is formed to include gas diffusion openings 36 and 38. Activated carbon film 32 stretches across semiconductor wafer 30 to allow gas to diffuse through it from openings 36 and 38 to the interior of the sensor, while preventing liquid from passing through. Hygroscopic material 34 is located in the interior of the sensor, and may, for example, include materials such as zeolites, alumina, other highly porous materials with affinity to water, polysulfonates, and/or dessicants such a DRIERITE® dessicant supplied by W.A. Hammond Drierite Co., to harvest (adsorb) water from the air and provide electrolyte to hydrate proton exchange membrane 20. First thin film subassembly 12 and second thin film subassembly 14 are attached together at outer portions thereof via a known method such as fusion bonding or another wafer bonding technique.

In operation, gas passes through openings 36 and 38 and diffuses through activated carbon film 32. CO in the gas interacts with the electrode stack formed by bottom electrode membrane 22, proton exchange membrane 20 and top electrode membrane 18 to produce an electrochemical reaction. The electrochemical reaction generates an electrical signal between bottom electrode membrane 22 and top electrode membrane 18 that is proportional to the concentration of CO at bottom electrode membrane 22. This electrical signal is detectable at contact pads 25 and 27 by virtue of their electrical connection to top electrode membrane 18 and bottom electrode membrane 22 by conductive vias 24 and 26, respectively. The electrical signal at contact pads 25 and 27 is processed and monitored by appropriate circuitry in a manner generally known in the art to indicate the level of CO present.

Figure 2:
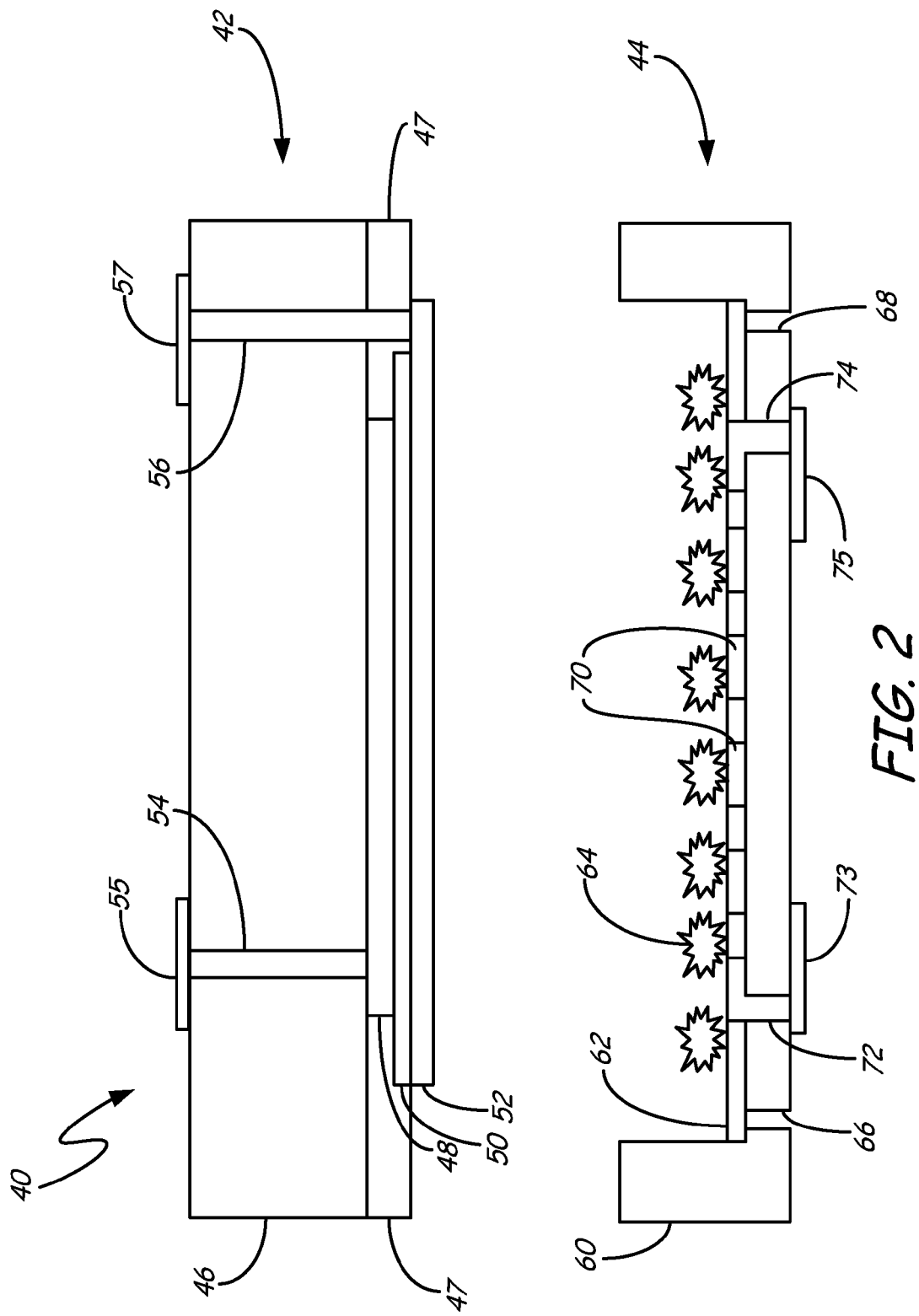
FIG. 2 is a diagram illustrating a thin film/MEMS gas sensor according to another embodiment of the present invention.

FIG. 2 is a diagram illustrating thin film gas sensor 40 according to another embodiment of the present invention. The description of sensor 40 that follows describes a particular embodiment in which sensor 40 is a CO sensor, although embodiments for detecting other target gases (such as toxic gases) will be similar in many respects. Sensor 40 includes first thin film subassembly 42 and second thin film subassembly 44. First thin film subassembly 42 is made up of semiconductor wafer 46, formed of silicon or a similar material, dielectric layer 47, and a membrane stack that includes top electrode membrane 48, proton exchange membrane 50, and bottom electrode membrane 52. Dielectric layer 47 may be composed of a material such as silicon dioxide ($SiO_2$), a silicon nitride ($Si_xN_y$) dielectric, or other polymeric dielectrics. Top electrode membrane 48 and bottom electrode membrane 52 are semi-permeable electrically conductive membranes, such as carbon membranes. Proton exchange membrane 50 may be a proton conductive membrane of a perfluorosulfate ionomer, for example, a NAFION® membrane supplied by DuPont, with composite catalytic electrodes. The composite catalytic electrodes include an electrode material coated with a catalyst coating that facilitates electrochemical reaction, reducing the energy required for the reaction to occur. For example, in a CO sensor, the catalyst coating is a platinum alloy. Conductive via 54 extends through semiconductor wafer 46 to provide electrical contact between top electrode membrane 48 and contact pad 55, and conductive via 56 extends through semiconductor wafer 46 and dielectric layer 47 to provide electrical contact between bottom electrode membrane 52 and contact pad 57. Contact pads 55 and 57 may be composed of a conductive metal such as aluminum, copper, nickel, gold, or others.

Second thin film subassembly 44 includes semiconductor wafer 60, a filter film realized in the exemplary embodiment shown in FIG. 2 as activated carbon film 62, and hygroscopic material 64. Semiconductor wafer 60 may be formed with the geometry shown by high resolution MEMS processing techniques such as reactive ion etching, chemical anisotropic etching, or others, and is formed to include gas diffusion openings 66 and 68. Activated carbon film 62 stretches across semiconductor wafer 60 to allow gas to diffuse through it from openings 66 and 68 to the interior of the sensor, while preventing liquid from passing through. Microheater 70 is integrated into activated carbon film 62, with electrical connection being provided by conductive via 72 through semiconductor wafer 60 to contact pad 73, and by conductive via 74 through semiconductor wafer 60 to contact pad 75. Contact pads 73 and 75 may be composed of a conductive metal such as aluminum, copper, nickel, gold, or others. Microheater 70 may be made using metallic traces, doped silicon, or doped polysilicon in exemplary embodiments. Hygroscopic material 64 is located in the interior of the sensor, and may, for example, include materials such as zeolites, alumina, other highly porous materials with affinity to water, polysulfonates, and/or dessicants such a DRIERITE® dessicant supplied by W.A. Hammond Drierite Co., to harvest (adsorb) water from the air and provide electrolyte to hydrate proton exchange membrane 50. First thin film subassembly 42 and second thin film subassembly 44 are attached together at outer portions thereof via a known method such as fusion bonding or another wafer bonding technique.

In operation, gas passes through openings 66 and 68 and diffuses through activated carbon film 62. Microheater 70 is controlled for operation to maintain the temperature of the CO sensor to be near the temperature of the gas diffusing into the sensor.

CO in the gas interacts with the electrode stack formed by bottom electrode membrane 52, proton exchange membrane 50 and top electrode membrane 48 to produce an electrochemical reaction. The electrochemical reaction generates an electrical signal between bottom electrode membrane 52 and top electrode membrane 48 that is proportional to the concentration of CO at bottom electrode membrane 52. This electrical signal is detectable at contact pads 55 and 57 by virtue of their electrical connection to top electrode membrane 48 and bottom electrode membrane 52 by conductive vias 54 and 56, respectively. The electrical signal at contact pads 55 and 57 is processed and monitored by appropriate circuitry in a manner generally known in the art to indicate the level of CO present.

Figure 3:
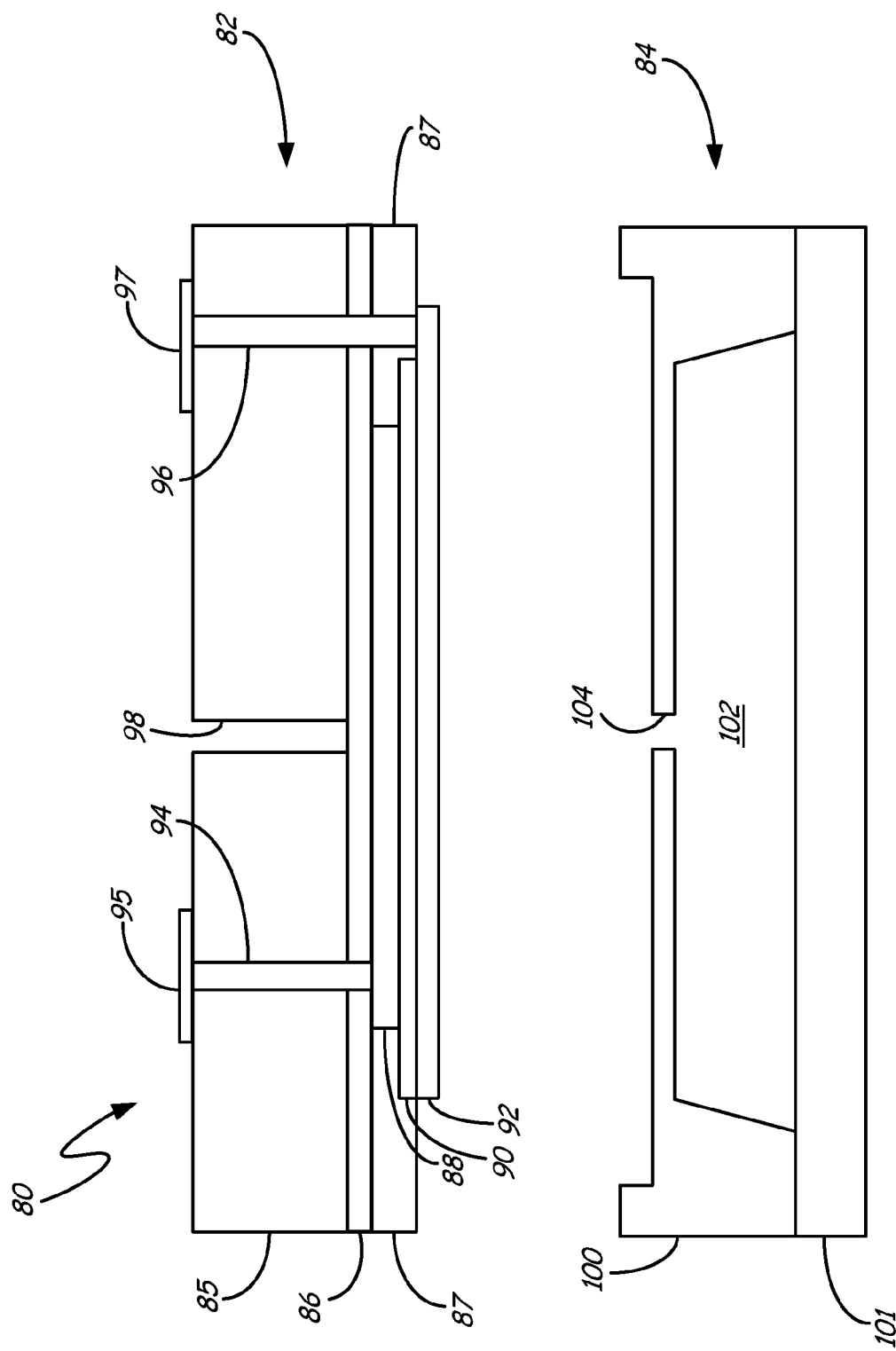
FIG. 3 is a diagram illustrating a thin film/MEMS gas sensor according to a further embodiment of the present invention.

FIG. 3 is a diagram illustrating thin film gas sensor 80 according to a further embodiment of the present invention. The description of sensor 80 that follows describes a particular embodiment in which sensor 80 is a CO sensor, although embodiments for detecting other target gases (such as toxic gases) will be similar in many respects. Sensor 80 includes first thin film subassembly 82 and second thin film subassembly 84. First thin film subassembly 82 is made up of semiconductor wafer 85, formed of silicon or a similar material, a filter film realized in the exemplary embodiment shown in FIG. 3 as activated carbon film 86, dielectric layer 87, and a membrane stack that includes top electrode membrane 88, proton exchange membrane 90, and bottom electrode membrane 92. Dielectric layer 87 may be composed of a material such as silicon dioxide ($SiO_2$), a silicon nitride ($Si_xN_y$) dielectric, or others. Top electrode membrane 88 and bottom electrode membrane 92 are semi-permeable electrically conductive membranes, such as carbon membranes. Proton exchange membrane 90 may be a proton conductive membrane of a perfluorosulfate ionomer, for example, a NAFION® membrane supplied by DuPont, with composite catalytic electrodes. The composite catalytic electrodes include an electrode material coated with a catalyst coating that facilitates electrochemical reaction, reducing the energy required for the reaction to occur. For example, in a CO sensor, the catalyst coating is a platinum alloy. Conductive via 94 extends through semiconductor wafer 85 to provide electrical contact between top electrode membrane 88 and contact pad 95, and conductive via 96 extends through semiconductor wafer 85 and dielectric layer 87 to provide electrical contact between bottom electrode membrane 92 and contact pad 97. Contact pads 95 and 97 may be composed of a conductive metal such as aluminum, copper, nickel, gold, or others. A gas diffusion path is formed to the membrane stack by gas diffusion opening 98, which allows gas to diffuse through activated carbon film 86 to top electrode membrane 88.

Second thin film subassembly 84 includes semiconductor wafers 100 and 101. Semiconductor wafer 100 may be formed with the geometry shown by high resolution MEMS processing techniques such as reactive ion etching, chemical anisotropic etching, or others. Semiconductor wafer 101 is formed to be complementary to semiconductor wafer 100, so that the two wafers may be attached (such as by fusion bonding or another known wafer bonding technique) to form reservoir 102. Reservoir 102 may have a depth between 10 and 500 micrometers (μm) in an exemplary embodiment. Semiconductor wafer 100 also includes hydration opening 104, which allows electrolyte (e.g., water) from reservoir 102 to evaporatively hydrate proton exchange membrane 90. First thin film subassembly 82 and second thin film subassembly 84 are attached together at outer portions thereof via a known method such as fusion bonding or another wafer bonding technique.

In operation, gas passes through openings 98 and diffuses through activated carbon film 86. CO in the gas interacts with the electrode stack formed by top electrode membrane 88, proton exchange membrane 90 and bottom electrode membrane 92 to produce an electrochemical reaction. The electrochemical reaction generates an electrical signal between top electrode membrane 88 and bottom electrode membrane 92 that is proportional to the concentration of CO at top electrode membrane 88. This electrical signal is detectable at contact pads 95 and 97 by virtue of their electrical connection to top electrode membrane 88 and bottom electrode membrane 92 by conductive vias 94 and 96, respectively. The electrical signal at contact pads 95 and 97 is processed and monitored by appropriate circuitry in a manner generally known in the art to indicate the level of CO present.

Various embodiments of thin film CO sensors are described above and shown in FIG. 1-3. The bodies of these sensors are composed of a semiconductor material, such as silicon or other materials, that can be processed by high resolution batch processing MEMS techniques. The sensors therefore have significantly smaller sizes than sensors constructed according to the current state of the art. For example, the thicknesses of the semiconductor wafers may be between about 25-550 micrometers (μm), the thicknesses of the top and bottom semi-permeable electrically conductive membranes may be between about 100 nanometers (nm) and 500 μm, the thickness of the proton exchange membrane may be between about 10 nm and 140 μm, the dielectric layer may be between about 1 nm and 640 μm, the activated carbon film may be between about 1-300 μm, the hygroscopic material may have sizes between about 10 nm and 10 μm, and the microheater (in the embodiment of FIG. 2) may have a thickness between about 100 nm and 5 μm. The contact pads may have thickness between about 100 nm and 5 μm. Thus, the total thickness of a sensor as disclosed herein may be less than about 3 millimeters (mm), and in many embodiments less than about 1 mm or even about 0.1 mm in thickness. This is a significant reduction in size in comparison to CO sensors constructed according to the state of the art, which are typically about 10 centimeters in thickness.

The CO sensor disclosed herein also may exhibit a significantly improved response time compared to sensors constructed according to the state of the art. The response time of a CO sensor is related to the length of the diffusion path for gas to travel through the sensor and the membrane stack of the sensor. The gas diffusion path in the CO sensor disclosed herein is significantly shorter than in sensors constructed according to the state of the art, resulting in a corresponding improvement in the response time of the sensor.

The CO sensor disclosed herein is also able to be constructed in a more structurally sound and consistent manner than many sensors of the prior art. Contact and alignment between the proton exchange membrane and the top and bottom electrode membranes in the membrane stack is consistently achieved by the thin film deposition of those layers (such as by a spin coating process, for example). This was not always the case in prior sensors, which pressed the electrodes and membrane together by crimping of the outer container.

The present invention has been described herein by illustrations of several embodiments of a CO sensor. It should be understood that the principles of the present invention are also applicable to a number of target gas sensors, such as sensors for detecting toxic gases such as propane, methane, ammonia, or others.

Although the present invention has been described with reference to preferred embodiments, workers skilled in the art will recognize that changes may be made in form and detail without departing from the spirit and scope of the invention.

The invention claimed is:

1. A thin film electrochemical target gas sensor, comprising:
 a body including a first subassembly and a second subassembly joined to form an interior portion of the body, the body being composed of a semiconductor material and including at least one opening configured to allow air to pass into the interior portion of the body;
 a membrane stack in the interior portion of the body, including first and second semi-permeable electrically conductive membranes and a proton exchange membrane therebetween that includes composite catalytic electrodes, the membrane stack producing an electrical signal that represents a concentration of the target gas in the air at the membrane stack;
 a filter film between the opening in the body and the membrane stack, the film being constructed to allow air to pass through to the membrane stack; and
 conductive contacts configured to provide electrical connection to the membrane stack to access the electrical signal produced by the membrane stack.

2. The sensor of claim 1, wherein the conductive contacts comprise:
 first and second contact pads on an exterior of the body;
 a first conductive via through the body electrically connecting the first contact pad to the first semi-permeable electrically conductive membrane; and
 a second conductive via through the body electrically connecting the second contact pad to the second semi-permeable electrically conductive membrane.

3. The sensor of claim 1, further comprising hygroscopic material located between the filter film and the membrane stack to adsorb water from air passing through the filter film and hydrate the membrane stack.

4. The sensor of claim 1, wherein the hygroscopic material comprises at least one material selected from the group consisting of zeolites, alumina, polysulfonates and dessicants.

5. The sensor of claim 1, further comprising a microheater integrated into the sensor.

6. The sensor of claim 5, further comprising:
 heater contact pads on the body of the sensor; and conductive vias extending through the body of the sensor to electrically connect the heater contact pads to the microheater.

7. The sensor of claim 1, further comprising a reservoir in the interior portion of the body of the sensor configured to hold water for hydrating the membrane stack.

8. The sensor of claim 1, wherein the sensor has a total thickness of less than 3 millimeters.

9. The sensor of claim 8, wherein the sensor has a total thickness of less than 1 millimeter.

10. The sensor of claim 9, wherein the sensor has a total thickness of less than 0.1 millimeters.

11. The sensor of claim 8, wherein the body has a total thickness of no greater than 1.1 millimeters.

12. The sensor of claim 1, wherein the body is composed of silicon.

13. The sensor of claim 1, wherein the sensor is configured to detect carbon monoxide (CO).

14. The sensor of claim 13, wherein the composite catalytic electrodes comprise a platinum alloy.

15. A thin film electrochemical target gas sensor, comprising:
    a body including a first subassembly, a second subassembly, and a third subassembly joined to form an interior portion of the body between the first and second subassemblies and a reservoir configured to contain a liquid between the second and third subassemblies, the body being composed of a semiconductor material and including at least one first opening in the first subassembly configured to allow air to pass into the interior portion of the body and at least one second opening in the second subassembly to allow moisture to pass from the reservoir to the interior portion of the body;
    a membrane stack in the interior portion of the body, including first and second semi-permeable electrically conductive membranes and a proton exchange membrane therebetween that includes composite catalytic electrodes, the membrane stack producing an electrical signal that represents a concentration of the target gas in the air at the membrane stack;
    a filter film between the opening in the body and the membrane stack, the film being constructed to allow air to pass through to the membrane stack; and
    conductive contacts configured to provide electrical connection to the membrane stack to access the electrical signal produced by the membrane stack.

16. The sensor of claim 15, wherein the conductive contacts comprise:
    first and second contact pads on an exterior of the body;
    a first conductive via through the body electrically connecting the first contact pad to the first semi-permeable electrically conductive membrane; and
    a second conductive via through the body electrically connecting the second contact pad to the second semi-permeable electrically conductive membrane.

17. The sensor of claim 15, wherein the sensor has a total thickness of less than 3 millimeters.

18. The sensor of claim 15, wherein the reservoir has a depth of no greater than about 0.5 millimeters.

19. The sensor of claim 15, wherein the sensor is configured to detect carbon monoxide (CO).

20. The sensor of claim 19, wherein the composite catalytic electrodes comprise a platinum alloy.

\* \* \* \* \*